United States Patent
Hu et al.

(10) Patent No.: US 10,818,011 B2
(45) Date of Patent: Oct. 27, 2020

(54) CARPAL SEGMENTATION AND RECOGNITION METHOD AND SYSTEM, TERMINAL AND READABLE STORAGE MEDIUM

(71) Applicant: SHENZHEN INSTITUTES OF ADVANCED TECHNOLOGY CHINESE ACADEMY OF SCIENCES, Shenzhen, Guangdong (CN)

(72) Inventors: Qingmao Hu, Guangdong (CN); Liyilei Su, Guangdong (CN); Xiaodong Zhang, Guangdong (CN); Xianjun Fu, Guangdong (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 78 days.

(21) Appl. No.: 16/236,366

(22) Filed: Dec. 29, 2018

(65) Prior Publication Data
US 2019/0206052 A1    Jul. 4, 2019

Related U.S. Application Data

(63) Continuation of application No. PCT/CN2018/070035, filed on Jan. 2, 2018.

(30) Foreign Application Priority Data

Dec. 29, 2017 (CN) .......................... 2017 1 1485720

(51) Int. Cl.
G06T 7/00     (2017.01)
G06T 7/13     (2017.01)
(Continued)

(52) U.S. Cl.
CPC ............ *G06T 7/0012* (2013.01); *A61B 6/505* (2013.01); *A61B 6/5217* (2013.01); *G06T 5/009* (2013.01);
(Continued)

(58) Field of Classification Search
CPC ......... G06T 5/40; G06T 7/143; G06T 7/0012; G06T 7/194; G06T 7/136;
(Continued)

(56) References Cited

U.S. PATENT DOCUMENTS 6,711,282 B1 *  3/2004  Liu ........................ G01N 23/04
                                                382/132
7,940,985 B2 *  5/2011  Sun ...................... G06K 9/4638
                                                382/155
(Continued)

FOREIGN PATENT DOCUMENTS

CN           101699511 A        4/2010

OTHER PUBLICATIONS

Liu, Bin, "Color segmentation method and system", CN 101699511, Machine translated, pp. 1-4. (Year: 2010).*

*Primary Examiner* — Yon J Couso
(74) *Attorney, Agent, or Firm* — Robert L. Stearns; Dickinson Wright PLLC

(57) ABSTRACT

The present application relates to the technical field of image recognition, and provides a carpal segmentation and recognition method, including: performing threshold segmentation on a carpal region of interest on a child orthotopic wrist X-ray image based on an adaptive threshold segmentation manner of variable threshold segmentation windows, and extracting edge information of the carpal region of interest based on an edge detection manner; combining a binarized image obtained by performing the threshold segmentation with the extracted edge information to obtain an initial
(Continued)

segmentation image; performing carpal recognition on the initial segmentation image by using a carpal anatomy priori model to obtain an initial recognition image including information of each carpal bone; and performing boundary optimization on the initial recognition image, and outputting a carpal recognition image obtained after the boundary optimization is performed.

12 Claims, 11 Drawing Sheets

(51) Int. Cl.
| | | |
|---|---|---|
| *A61B 6/00* | (2006.01) | |
| *G06T 7/143* | (2017.01) | |
| *G06T 5/00* | (2006.01) | |
| *G06T 7/194* | (2017.01) | |
| *G06T 7/12* | (2017.01) | |
| *G06T 5/40* | (2006.01) | |
| *G06T 7/136* | (2017.01) | |

(52) U.S. Cl.
CPC .............. *G06T 5/40* (2013.01); *G06T 7/12* (2017.01); *G06T 7/13* (2017.01); *G06T 7/136* (2017.01); *G06T 7/143* (2017.01); *G06T 7/194* (2017.01); *G06T 2207/10116* (2013.01); *G06T 2207/30008* (2013.01)

(58) Field of Classification Search
CPC . G06T 2207/30008; G06T 2207/10116; G06T 7/12; G06T 7/13; G06T 5/009; A61B 6/505; A61B 6/5217
See application file for complete search history.

(56) References Cited

U.S. PATENT DOCUMENTS

| | | | |
|---|---|---|---|
| 9,286,505 B2* | 3/2016 | Ajemba | G06T 7/0012 |
| 10,079,071 B1* | 9/2018 | Lay | G06K 9/4642 |
| 2007/0081713 A1* | 4/2007 | Jerebko | G06T 7/0012 |
| | | | 382/128 |

* cited by examiner

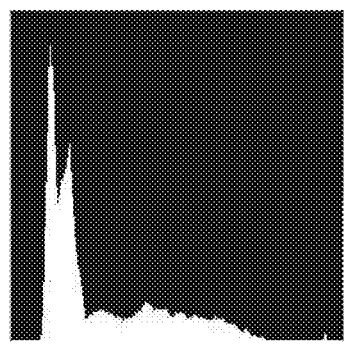
FIG.4
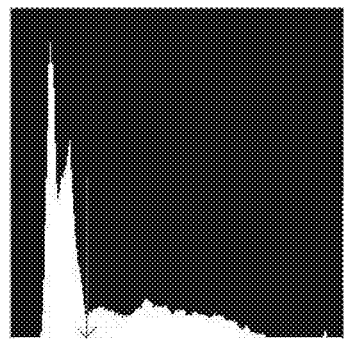
FIG.5
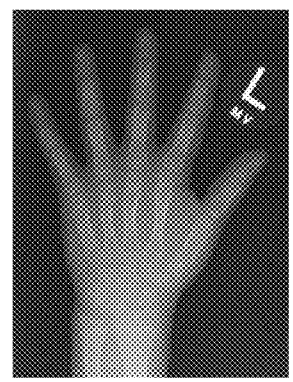 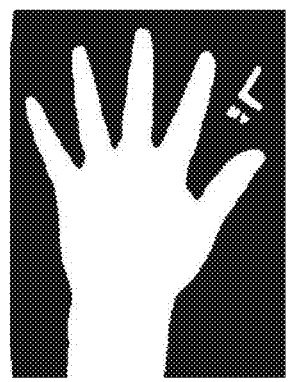
FIG.6a				FIG.6b

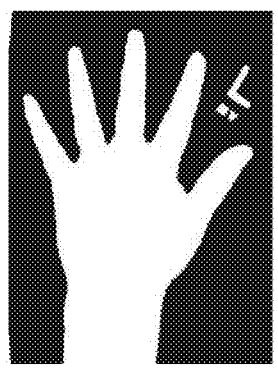 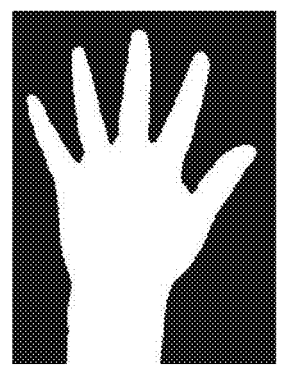 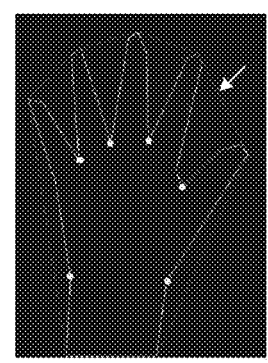
FIG.7a  FIG.7b  FIG.7c
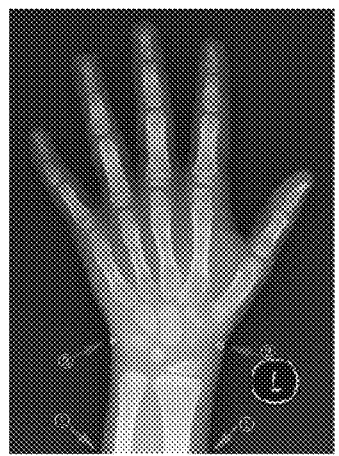 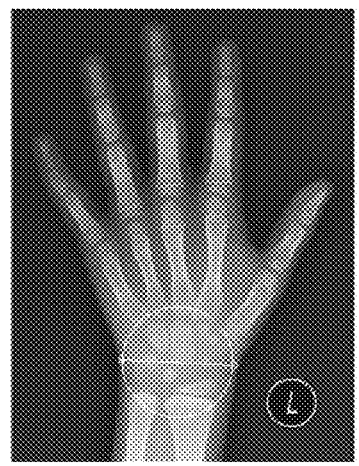 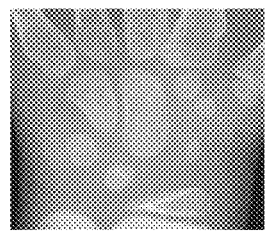
FIG.8a  FIG.8b  FIG.8c
FIG.9

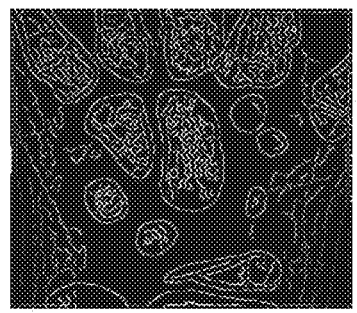
FIG.10a
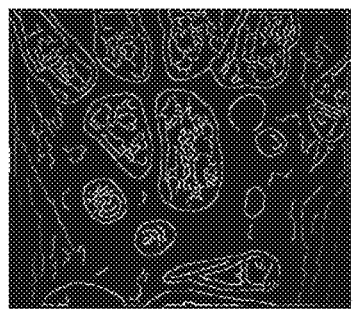
FIG.10b
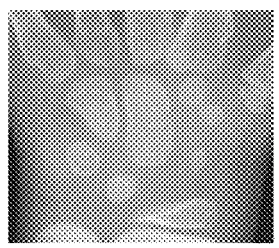
FIG.11a
FIG.11b
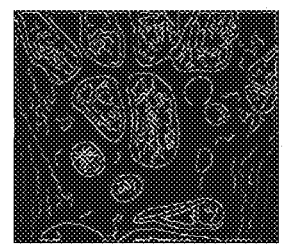
11c
FIG.11d
FIG.11e
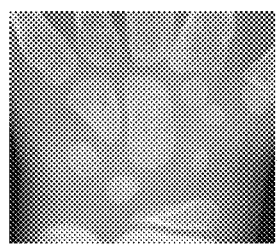
FIG.12a
FIG.12b
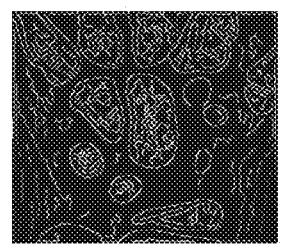
FIG.12c

FIG.12d  FIG.12e
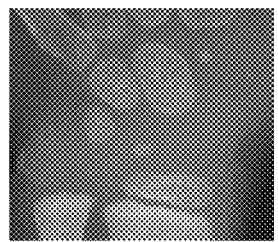
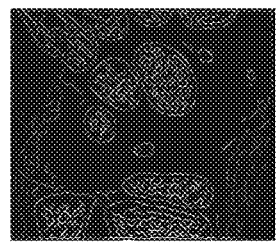
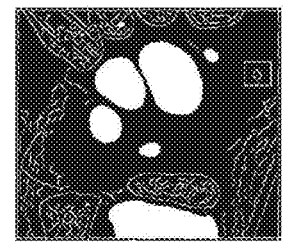
FIG.13a  FIG.13b  FIG.13c
FIG.13d  FIG.13e
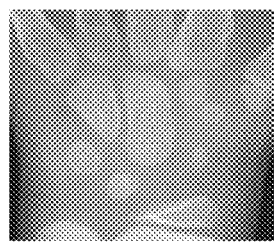
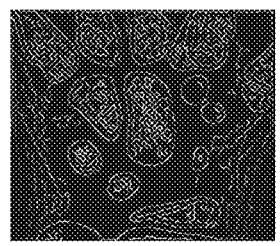
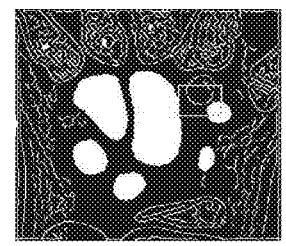
FIG.14a  FIG.14b  FIG.14c
FIG.14d  FIG.14e

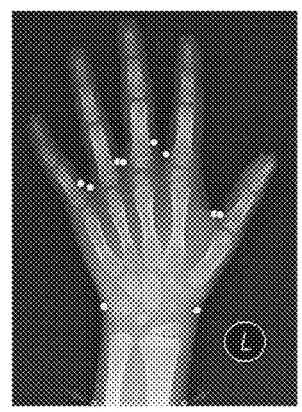 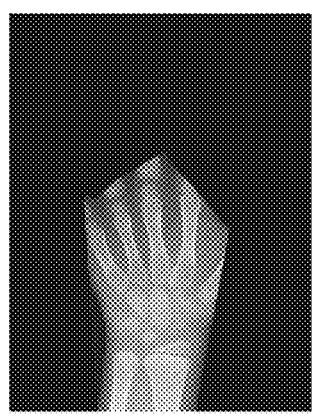 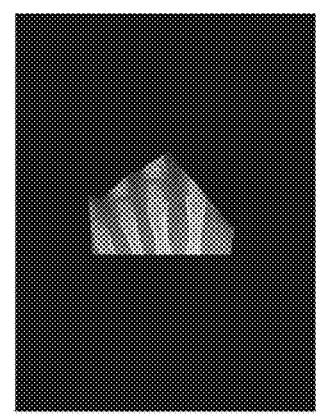
FIG.18a  FIG.18b  FIG.18c
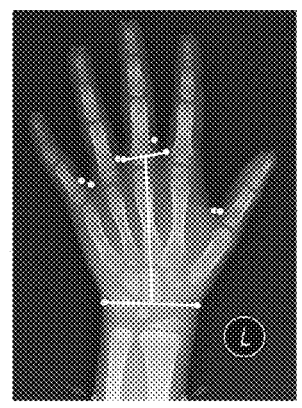 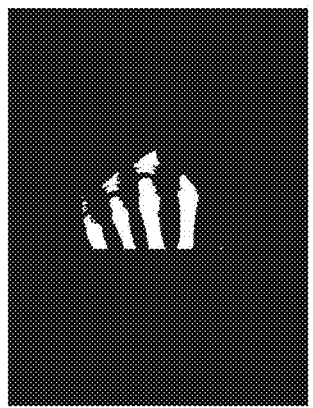 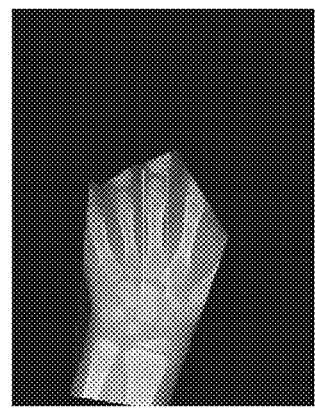
FIG.19a  FIG.19b  FIG.19c
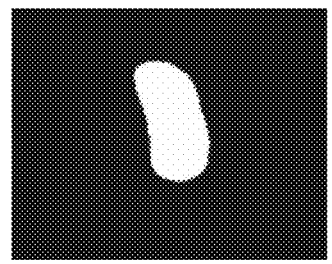 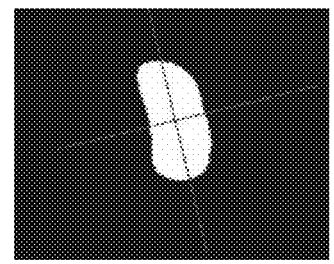
FIG.20a  FIG.20b
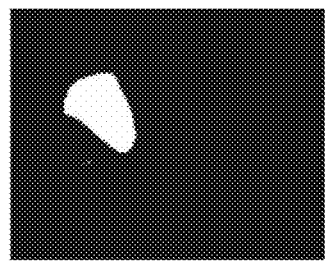 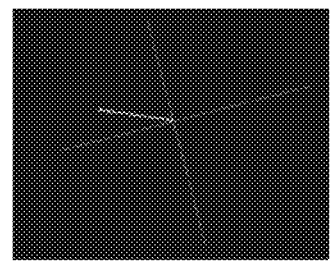
FIG.21a  FIG.21b

FIG.22a          FIG.22b
FIG.22c          FIG.22d
FIG.23
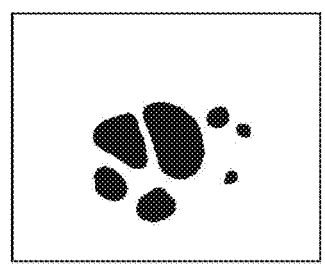
FIG.24

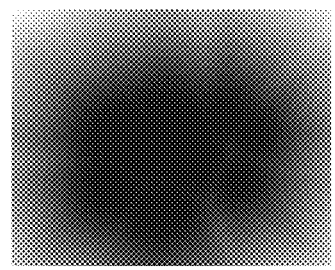
FIG.25
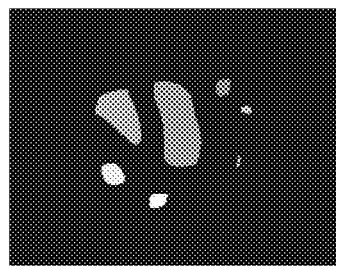 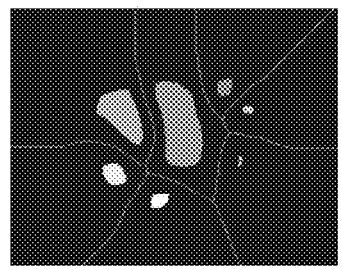
FIG.26aFIG.26b
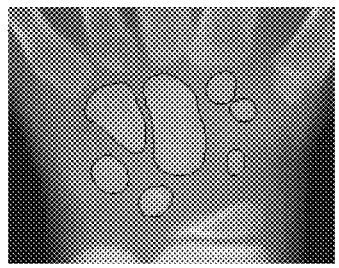
FIG.27
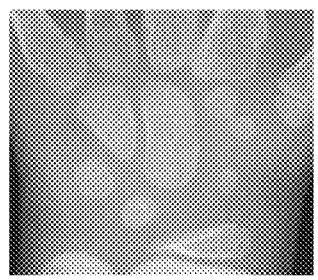 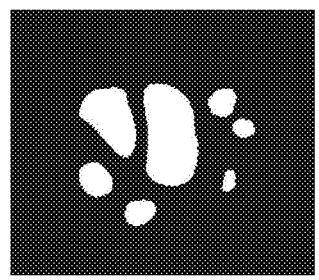 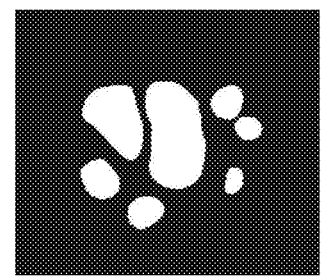
FIG.28aFIG.28bFIG.28c

CARPAL SEGMENTATION AND RECOGNITION METHOD AND SYSTEM, TERMINAL AND READABLE STORAGE MEDIUM

CROSS REFERENCE TO RELATED APPLICATIONS

The present application is a Continuation Application of PCT Application No. PCT/CN2018/070035 filed on Jan. 2, 2018, which claims the benefit of Chinese Patent Application No. 201711485720.1 filed on Dec. 29, 2017. All the above are hereby incorporated by reference.

TECHNICAL FIELD

The present application belongs to the technical field of image recognition, and particularly relates to a carpal segmentation and recognition method and system, a terminal and a readable storage medium.

BACKGROUND

The skeletal development age (abbreviated as a skeletal age) generally refers to a development age obtained by comparing a development level of skeletons in adolescents and children with skeletal development standards. The skeletal age largely represents a true developmental level of the children, and is used to determine the maturity of a human body more accurately than the actual age. The skeletal age assessment is to study the occurrence of an ossification point, and a relationship between fusion time of epiphysis and backbone and the actual age. At the time of the assessment, X-ray examination is performed on a non-principal hand from distal ends of the ulna and the radius to a distal end of the phalanx, so as to estimate the skeletal development age from an image. The difference in the skeletal age and a physiological age may reflect whether the skeletal development is normal or not. Therefore, the skeletal age is one of main reference indicators in the diagnosis of pediatric endocrine diseases, the assessment of children's growth and development, the selection of athletes and the forensic medicine.

For girls under 6 years of age and boys under 8 years of age, carpal bones are an important region for the skeletal age recognition, because there is a large amount of growth and development information in carpal regions for young children in this age group. Recognizing the number and the shape of the carpal bones is a relatively stable and effective method before the carpal bones overlap mutually.

The carpal bone regions of young children have uncertainties, mainly characterized as follows: 1) uncertainty in the number of the carpal bones in young children; 2) obscure boundary, wherein a contrast of the carpal bones with a region of soft tissues around them is not obvious; 3) uneven density of the carpal bones and the soft tissues around them, these uncertainties make it difficult to segment the carpal region. At present, the segmentation and recognition of the carpal region is not effective in a single method, for example, it is impossible to accurately segment the shapes of the carpal bones due to the obscure boundary with the region of the soft tissues around the carpal bones, or it is difficult to extract some special carpal bones (for example, carpal bones at calcification points or carpal bones with smaller shapes).

SUMMARY

The technical problem to be solved by the present application is to provide a carpal segmentation and recognition method and system, a terminal and a readable storage medium, which aim to solve problems of difficulty and/or inaccuracy in segmentation and recognition of a carpal region in the prior art.

The present application is achieved by a carpal segmentation and recognition method, including:

performing threshold segmentation on a carpal region of interest on a child orthotopic wrist X-ray image based on an adaptive threshold segmentation manner of variable threshold segmentation windows, and extracting edge information of the carpal region of interest based on an edge detection manner;

combining a binarized image obtained by performing the threshold segmentation with the extracted edge information to obtain an initial segmentation image;

performing carpal recognition on the initial segmentation image by using a carpal anatomy priori model to obtain an initial recognition image including information of each carpal bone; and performing boundary optimization on the initial recognition image, and outputting a carpal recognition image obtained after the boundary optimization is performed.

The present application further provides a carpal segmentation and recognition system, including:

a processing unit, which is configured to perform threshold segmentation on a carpal region of interest on a child orthotopic wrist X-ray image based on an adaptive threshold segmentation manner of variable threshold segmentation windows, and extract edge information of the carpal region of interest based on an edge detection manner, and combine a binarized image obtained by performing the threshold segmentation with the extracted edge information to obtain an initial segmentation image;

a recognition unit, which is configured to perform carpal recognition on the initial segmentation image by using a carpal anatomy priori model to obtain an initial recognition image including information of each carpal bone; and an optimization unit, which is configured to perform boundary optimization on the initial recognition image, and output a carpal recognition image obtained after the boundary optimization is performed.

One embodiment of the present application provides a terminal, including a memory, a processor, and a computer program stored on the memory and running on the processor, wherein the processor, when executing the computer program, implement various steps in the carpal segmentation and recognition method as described above.

Another embodiment of the present application further provides a readable storage medium storing a computer program thereon, and the computer program, when being executed by the processor, implements various steps in the carpal segmentation and recognition method as described above.

Compared with the prior art, the present application has the beneficial effects that an initial segmentation image is obtained by performing adaptive threshold segmentation and edge extraction based on variable threshold segmentation windows on a carpal region of interest, and carpal recognition is performed on the initial segmentation image by using a carpal anatomy priori model to obtain an initial recognition image including information of each carpal bone, boundary optimization is performed on the initial recognition image, and finally an optimized carpal recognition image is output. The embodiments of the present application combine the adaptive threshold segmentation manner based on the variable threshold segmentation windows with edge extraction, and retain advantages of two image processing methods, and avoids under-segmentation and over-segmentation caused by the use of a single method in carpal segmentation, thereby obtaining the initial carpal segmentation with higher accuracy. The carpal recognition and the boundary optimization are performed through a pre-trained carpal anatomy priori model on the basis of obtaining an initial carpal segmentation result, and finally the carpal recognition image with high segmentation accuracy is output. Compared with prior art, the embodiments of the present application improve the automatic segmentation and recognition accuracy of the carpal region.

BRIEF DESCRIPTION OF THE DRAWINGS

FIG. 4 is a grayscale histogram of a full palm image of an image to be recognized according to an embodiment of the present application.

FIG. 5 is a schematic diagram of a boundary between grayscale values of a background and a foreground according to an embodiment of the present application.

FIGS. 6a and 6b are schematic diagrams of palm binarization according to an embodiment of the present application.

FIGS. 7a to 7c are schematic diagrams of removing irrelevant information in a palm binarized image according to an embodiment of the present application.

FIGS. 8a to 8c are schematic diagrams of extracting a carpal region of interest according to an embodiment of the present application.

FIG. 9 is a binarized image obtained by performing threshold segmentation on a carpal region of interest according to an embodiment of the present application.

FIGS. 10a and 10b are schematic diagrams of performing Canny edge extraction on a carpal region of interest according to an embodiment of the present application.

FIGS. 11a to 11e are schematic diagrams of performing hole filling and eroding of an over-segmented binarized image according to an embodiment of the present application.

FIGS. 12a to 12e are schematic diagrams of performing hole filling and eroding on an under-segmented binarized image according to an embodiment of the present application.

FIGS. 13a to 13e and FIGS. 14a to 14e are schematic diagrams of different carpal bones obtained by combining a binarized image and edge information according to an embodiment of the present application.

FIGS. 18a to 18c are schematic diagrams of intercepting an image of a distal end of a metacarpal bone according to an embodiment of the present application.

FIGS. 19a to 19c are schematic diagrams of positioning of a metacarpal bone according to an embodiment of the present application.

FIGS. 20a and 20b are schematic diagrams of establishing a Cartesian coordinate system according to a capitate bone according to an embodiment of the present application.

FIGS. 21a and 21b are schematic diagrams of determining a reference distance according to a hamate bone according to an embodiment of the present application.

FIGS. 22a to 22d are schematic diagrams of obtaining an initial recognition image according to an embodiment of the present application.

FIG. 23 is a gradient image according to an embodiment of the present application.

FIG. 24 is a schematic diagram of a negation result of an initial recognition image according to an embodiment of the present application.

FIG. 25 is a distance image according to an embodiment of the present application.

FIGS. 26a and 26b are marked images obtained by fusing a foreground marked image and a foreground marked image according to an embodiment of the present application.

FIG. 27 is a schematic diagram of an outline of performing watershed segmentation on FIG. 15.

FIGS. 28a to 28c are schematic diagrams of segmentation of a carpal region including seven carpal bones according to an embodiment of the present application.

DESCRIPTION OF THE EMBODIMENTS

In order to make objectives, technical solutions and advantages of the present application be clearer, the present application will be further described in detail below with reference to accompanying drawings and embodiments. It should be understood that specific embodiments described herein are merely illustrative of the present application and are not intended to limit the present application.

Figure 1:
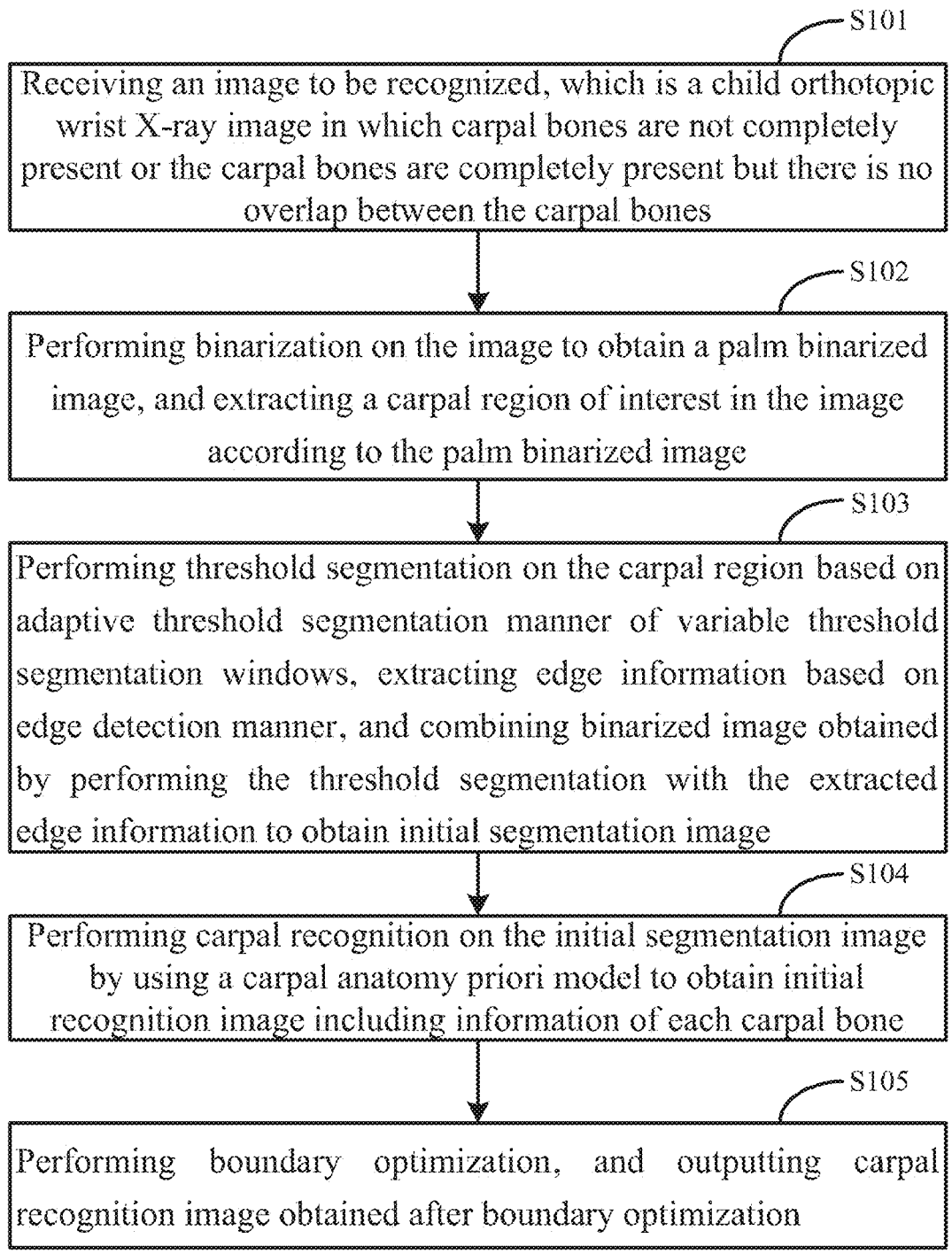
FIG. 1 is a flow diagram of a carpal segmentation and recognition method according to an embodiment of the present application.

In order to automatically recognize and segment carpal regions of young children (girls under 6 years old and boys under 8 years old), improve the segmentation accuracy of the carpal regions, and provide the guidance for the application of the carpal region in the automatic skeletal age recognition, an embodiment of the present application provides a carpal segmentation and recognition method as shown in FIG. 1, including:

S101, receiving an image to be recognized, wherein the image to be recognized is a child orthotopic wrist X-ray image in which carpal bones are not completely present or the carpal bones are completely present but there is no overlap between the carpal bones;

S102, performing binarization on the image to be recognized to obtain a palm binarized image, and extracting a carpal region of interest in the image to be recognized according to the palm binarized image;

S103, performing threshold segmentation on the carpal region of interest based on an adaptive threshold segmentation manner of variable threshold segmentation windows, and extracting edge information of the carpal region of interest based on an edge detection manner, and combining a binarized image obtained by performing the threshold segmentation with the extracted edge information to obtain an initial segmentation image;

S104, performing carpal recognition on the initial segmentation image by using a carpal anatomy priori model to obtain an initial recognition image including information of each carpal bone; and S105, performing boundary optimization on the initial recognition image, and outputting a carpal recognition image obtained after the boundary optimization is performed.

The embodiments of the present application calculate an initial carpal region by a method of combining adaptive thresholds of variable threshold segmentation windows with edge information based on existing sample data, recognizes each carpal bone from the initial region by learning and establishing a carpal anatomy priori model, and finally optimizes a carpal boundary based on a marked watershed segmentation method, so as to realize accurate segmentation of carpal bones of a young child.

The embodiments of the present application provide a method for segmenting carpal bones of a young child by combining an adaptive threshold segmentation of variable threshold segmentation windows with edge information. After data is preprocessed, the embodiment of the present application implements segmentation of the carpal region through five stages.

1. Adaptive threshold segmentation of the variable threshold segmentation windows. A window centered on each pixel point is determined based on contrast information of grayscale values within variable windows, and a threshold value within each window is solved to perform threshold segmentation on the carpal region of interest.

2. Combination of the edge information with a threshold segmentation result. A Canny edge detection method is used to extract outline information from an original image of the carpal region of interest, and a result is combined with the threshold segmentation result to obtain an initial segmentation image, the carpal bones are recognized by utilizing the carpal anatomy priori model learned from training, and initial segmentation of the carpal bones is achieved.

3. Construction of the carpal anatomy priori model. The carpal bones are recognized from the initial segmentation image in a supervised manner by using anatomical knowledge of the carpal bones and their centre-of-gravity positions are extracted, a Cartesian coordinate system of the carpal region is established with the center of gravity of the capitate bone as the origin, and a distance between the capitate bone and the hamate bone serves as a reference distance, and a ratio of the distance from the remaining bones of the carpal region to the capitate bone to the reference distance and angle information of the center of gravity of each bone in the Cartesian coordinate system are obtained. Finally, the anatomy priori model of the carpal region is obtained by statistical analysis on a large amount of data.

4. Recognition of the carpal bones. The carpal bones are recognized by the carpal anatomy priori model: firstly, a centre-of-gravity position of the capitate bone and its long and short axis directions are determined from the initial segmentation image by using information about the metacarpal bone, position information of the hamate bone is determined according to the position of the capitate bone to obtain the reference distance, and finally, other carpal bones are recognized by utilizing a position range of the remaining carpal bones given in the model to obtain the initial recognition image.

5. Accurate segmentation of the carpal bones, which is realized for the initial recognition image of the carpal bones by using the marked watershed segmentation method.

Figure 2:
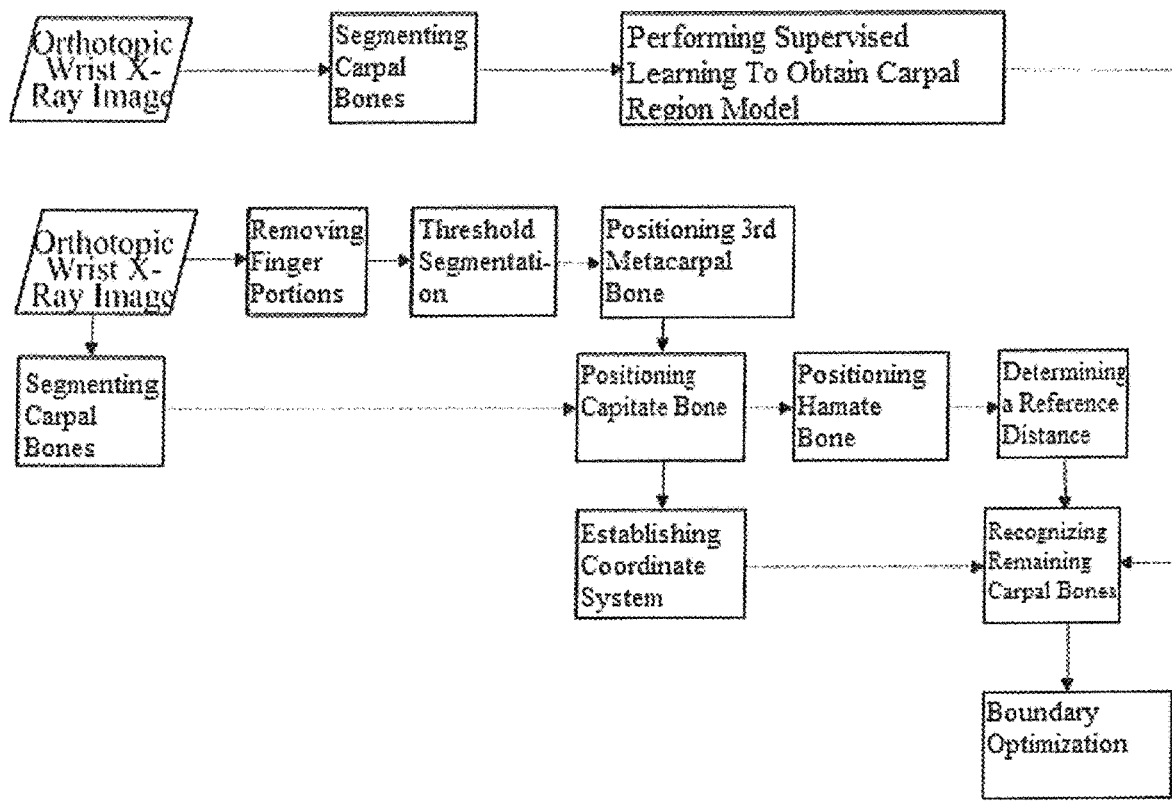
FIG. 2 is a detailed flow diagram of a carpal segmentation and recognition method according to an embodiment of the present application.

Based on the above description, a detailed process of a carpal segmentation and recognition method according to an embodiment of the present application is shown in FIG. 2, and the following further describes the embodiment of the present application.

An Image to be Recognized

Figures 3A, 3B, 3C:
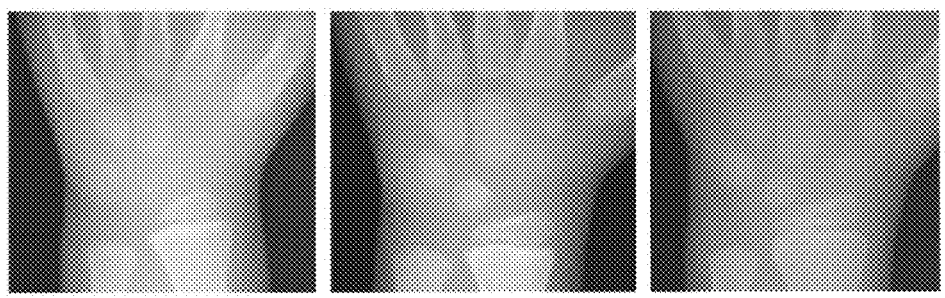
FIGS. 3a to 3c are child orthotopic wrist X-ray images in which carpal bones are not completely present or the carpal bones are completely present but there is no overlap between the carpal bones according to an embodiment of the present application.

The image to be recognized in the embodiment of the present application is a child orthodontic wrist X-ray image of a young child, and FIG. 3a to FIG. 3c respectively show different children orthodontic wrist X-ray images, it is necessary for the child orthodontic wrist X-ray image in the young child to completely include all the bone information which have been shown in distal ends of the ulna and the radius of the hand, as well as a carpal region of a non-primary hand and a metacarpal and phalanx region.

Since the embodiment of the present application segments and extracts the carpal bones of the young child, only an image in which the carpal bones are not completely present or completely present but there is no overlap between the carpal bones is used in the embodiment of the present application.

Extraction of the Carpal Region of Interest (CROI), Including:

1: Binarization of the Child Orthodontic Wrist X-ray Image:

In the embodiment of the present application, it is first necessary to perform binarization on the child orthodontic wrist X-ray image.

In particular, it is necessary to use outline information of the palm for positioning the CROI. According to characteristics of the child orthodontic wrist X-ray image, its grayscale histogram is roughly divided into two parts, namely, one part with smaller grayscale value serves as a background and one part with larger grayscale value serves as a palm, and the image is binarized by using the minimum value located between the two parts in the grayscale histogram. For each image I to be recognized, the following processing is performed:

1) the grayscale histogram H in the image I to be recognized is counted, and the grayscale histogram H is as shown in FIG. 4;

2) a valley point, such as a valley point pointed by an arrow in FIG. 5, with the highest slope from valley points to their adjacent peaks in the grayscale histogram H is calculated; and 3) a grayscale value of the valley point is set as a threshold value, and the image is binarized to obtain a palm binarized image including an outline of the palm. FIG. 6a is the image I to be recognized, and FIG. 6b is the palm binarized image obtained after the image I to be recognized in FIG. 6a is binarized.

2. Removal of Irrelevant Information in the Palm Binarized Image.

Text information about the child orthodontic wrist X-ray image is usually marked in the child orthodontic wrist X-ray image, and grayscale values of these pieces of information are generally high, and segmented out when the child orthodontic wrist X-ray image is binarized.

Since an area of the marked information is small, it is only necessary to find the largest connected region in all the white regions in the palm binarized image obtained after the binarization is performed, and delete the remaining white regions, resulting in the palm binarized image in which the irrelevant information is removed. As shown in FIG. 7, FIG. 7a is a palm binarized image in which irrelevant information is not removed, FIG. 7b is a palm binarized image in which irrelevant information is removed, and FIG. 7c is an image obtained by calculating recessed points of the palm binarized image after the irrelevant information is removed.

3. Positioning of a Wrist Line and Determination of the CROI

The carpal region is distributed near the wrist. Analysis of the outline of the palm shows that there is a large width change at an intersection of the arm and the palm. The outline of the palm in the palm binarized image is extracted, and an approximate polygon of the outline of the palm is solved, the maximum distance between the approximate polygon and the original outline is selected as 8 pixel points, and then convex hulls of the approximate polygon are obtained, as shown in an arrow in FIG. 7c, a plurality of concave portions are formed between the convex hulls and the approximate polygon, and a point at which each concave portion is at a maximum distance from the adjacent convex hull is found, and the points at which the concave portions are at the maximum distance from the adjacent convex hulls are the concave points corresponding to the concave portions, that is, points represented by all white circles of FIG. 7c. the concave points of the outline of the palm are searched in a clockwise or counterclockwise direction from an interception point on either side of the lowermost end of the image to be recognized (as indicated by an arrow ① in FIG. 8a), the searched first recessed point and the searched last concave point are two ends of the wrist (as indicated by an arrow ② in FIG. 8a).

A circumscribed circle is made by using a straight segment in which a connecting line of the two concave points intersect the palm region as a diameter, as shown in FIG. 8b, and a circumscribed square of the circumscribed circle is made, sides of the circumscribed square are parallel or vertical to the horizontal axis of the image, the resulting square contains all the carpal bones as well as distal ends of partial ulnas and radiuses, and a proximal end of the metacarpal bone, and serves as the CROI, and the CROI is as shown in FIG. 8c.

Segmentation Within the CROI

1. Threshold Segmentation

Since the density of the carpals and soft tissues around the carpal bones is not uniform, the contrast between the early developing carpal bones and soft tissues around the carpal bones is low, and the size of the carpal bones is unknown, a global threshold or a local threshold of a fixed window size cannot be used for segmenting the carpal bones. In the embodiment of the present application, an adaptive threshold segmentation manner of variable threshold segmentation windows is adopted for performing threshold segmentation on the CROI.

In the simplest case, assuming that there are only two grayscales B and G in a region, wherein if a ratio of the grayscale B is p, then a grayscale standard deviation of the region is $\sqrt{p(1-p)}|G-B|$, and the standard deviation is proportional to $|G-B|$. When the ratios of the two grayscales in the window are the same, the standard deviation reaches a maximum of $0.5|G-B|$, and when p or (1−p) falls to 0.1, the standard deviation is $0.3|G-B|$, which is 0.6 times the maximum value. Therefore, a threshold segmentation method based on adaptive variable windows will be adopted: for each pixel (x, y) in the image, a center of its corresponding window is located at (x, y), and the window has a width of W (x, y) and a height of H(x, y). In each image, the maximum standard deviation $sd_{max}$ of the grayscales in all possible windows is found. For each pixel (x, y), the minimum window that makes a standard deviation sd of grayscales in the windows centered on the pixel point not less than $0.6*sd_{max}$ is found and satisfies W(x, y)=H(x, y), wherein for each pixel (x, y), an average of the grayscales and a standard deviation are calculated in the window centered on it and having the height of H (x, y) and the width of W (x, y), all the (x, y) and possible windows are calculated and compared to obtain the maximum standard deviation, which is denoted as $sd_{max}$.

After the window corresponding to each pixel point is determined, a threshold formula is used within each window:

$$T(x, y) = m(x, y) * \left(1 + k * \frac{sd}{1.2 * sd_{max}}\right)$$

A threshold is obtained by calculation, wherein m(x, y) represents an average of the grayscales in the window, and k represents an experimentally determined constant, which is a constant between 0.04 and 0.08 in this embodiment, T(x, y) represents a grayscale threshold of the pixel (x, y). The threshold segmentation is a transformation from an original grayscale image I(x, y) to a binary image B(x, y). When I(x, y)<T(x, y), B(x, y) is 0, otherwise B(x, y) is 1, wherein 0 represents a background and 1 represents a foreground. A binarized image obtained by performing threshold segmentation on the CROI by the adaptive threshold segmentation manner of the variable threshold segmentation windows is shown in FIG. 9.

2. Edge Extraction

In the embodiment of the present application, all edge information in the CROI is extracted by using a Canny edge detection method. The Canny edge detection method includes the following steps: 1) smoothing the CROI by using a Gaussian filter; 2) calculating a gradient magnitude and a gradient direction by using a first-order partial derivative finite difference; 3) performing non-maximum suppression on the gradient amplitude; and 4) testing and joining edges by using a double-threshold algorithm.

In the embodiment of the present application, a Gaussian filter with a size of 3*3 and a σ of 1 is used to smooth the CROI, and then a Sobel operator of 5*5 is used to calculate the gradient amplitude and the gradient direction, and the Sobel operator of 5*5 has a form as follows:

| Horizontal Direction | | | | |
|---|---|---|---|---|
| 2 | 3 | 0 | −3 | −2 |
| 3 | 4 | 0 | −4 | −3 |
| 6 | 6 | 0 | −6 | −6 |
| 3 | 4 | 0 | −4 | −3 |
| 2 | 3 | 0 | −3 | −2 |
| Vertical Direction | | | | |
| 2 | 3 | 6 | 3 | 2 |
| 3 | 4 | 6 | 4 | 3 |
| 0 | 0 | 0 | 0 | 0 |
| −3 | −4 | −6 | −4 | −3 |
| −2 | −3 | −6 | −3 | −2 |

A first hysteresis threshold (high threshold) in the Canny edge detection is selected as 210, or determined by an adaptive method (Saheba S M, Upadhyaya T K, Sharma R K. Lunar surface crater topology generation using adaptive edge detection algorithm. IET Image Processing 2016 10(9): 657-661), and a second hysteresis threshold is taken as ⅓ of the high threshold. The obtained result image also contains a large number of small segments; and after the areas and the lengths of all the segments in an edge detection result are analyzed, the segments whose areas are smaller than 1 mm$^2$ are regarded as interference segments for being removed, and finally the edge information is obtained. FIG. 10a shows an image obtained by employing Canny edge extraction for the CROI, and FIG. 10b shows an image with partial shorter interference segments removed.

3. Combination of the Edge Information with the Threshold Segmentation Result:

The specific implementation method is as follows.

1) In the threshold segmentation result, if partial soft tissues and the carpal bones are not separated due to higher grayscale values of the soft tissues around the carpal bones, there is no over-segmentation. After the edge information is obtained, if a pixel in which an edge is located serves as a foreground in the binarized image, the pixel is set as a background. After hole filling is performed, the binary image is 3*3 eroded, an interval between the connected regions is increased, and partial single pixel points and single-pixel-wide segments in the binary image are removed; FIG. 11a is a CROI, FIG. 11b is a binarized image obtained by performing the threshold segmentation on the CROI, wherein there is an over-segmented portion in a block; FIG. 11c is a result obtained by performing the Canny edge extraction on the CROI; FIG. 11d is a result by superimposing the edge information on the over-segmented portion of the binarized image; and FIG. 11e is an initial segmentation result after hole filling and eroding are performed.

2) If a binarized carpal region is incomplete due to uneven density in the carpal bones or low grayscale values of partial regions in the carpal bones, there is under-segmentation. After the edge information is obtained, if a pixel in which the edge is located serves as a background in the binarized image, the pixel in the binarized image is set as a foreground, that is, the edges are added. After the edge information is added, the hole filling is performed, and the binary image is 3*3 eroded, the interval between the connected regions is increased, and partial single pixel points and single-pixel-wide segments in the binary image are removed. FIG. 12a is a CROI, and FIG. 12b is a binarized image obtained by performing the threshold segmentation on the CROI, wherein there is an under-segmented portion in a block; FIG. 12c is a result obtained by performing the Canny edge extraction on the CROI, FIG. 12d shows a result obtained by superimposing the edge information on the over-segmented portion of the binarized image; and FIG. 12e shows an initial segmentation result after the hole filling and eroding are performed.

3) Since the density of the soft tissues around the carpal bones are uneven and the carpal bones are blurred at a calcification point and edges of an ossification center stage, the Canny edge detection result of the carpal bones may be discontinuous and the segments are determined as the interference segments due to too small areas, or the edges of the carpal bones are fully expressed; the threshold segmentation may better express the carpal information in such cases; and the Canny edge detection extracts more edge information inside the carpal bones, the presence of these edges does not recognize the carpal bones and will have a certain influence on the recognition of the carpal bones, and the threshold segmentation result of the carpal bones is a form of the connected regions in the expression of the carpal bones, and the combination of the two may play a complementary role.

FIG. 13 and FIG. 14 are schematic diagrams of different carpal bones obtained by combining a binarized image and edge information according to an embodiment of the present application, respectively.

In particular, FIG. 13a is an image of a carpal region of interest; FIG. 13b is a Canny edge extraction result; FIG. 13c shows that a Canny edge extraction result is subjected to closed outline filling to show incomplete edge segments; FIG. 13d shows that edge information is superimposed into the binarized image, wherein carpal information is mainly expressed by a threshold segmentation result; and FIG. 13e is an initial segmentation result obtained after hole filling and erosion are performed; and FIG. 14a is an image of a carpal region of interest; FIG. 14b is a Canny edge extraction result of the carpal region of interest; FIG. 14c shows that a trapezoid bone has a discontinuous edge and one segment is regarded as an interference segment to be removed due to short length; FIG. 14d shows that edge information is superimposed into a binarized image, carpal information is mainly expressed by a threshold segmentation result; and FIG. 14e is an initial segmentation result obtained after hole filling and erosion are performed.

Establishment of a Carpal Anatomy Priori Model

Distal ends of partial ulnas and radiuses and proximal ends of partial metacarpal bones may also be included in the carpal region of interest obtained in the embodiment of the present application in addition to the carpal bones. However, all bone blocks not belonging to the carpal bones are located around the region of interest, and most of the bone blocks are non-quasi-circular.

Figure 15:
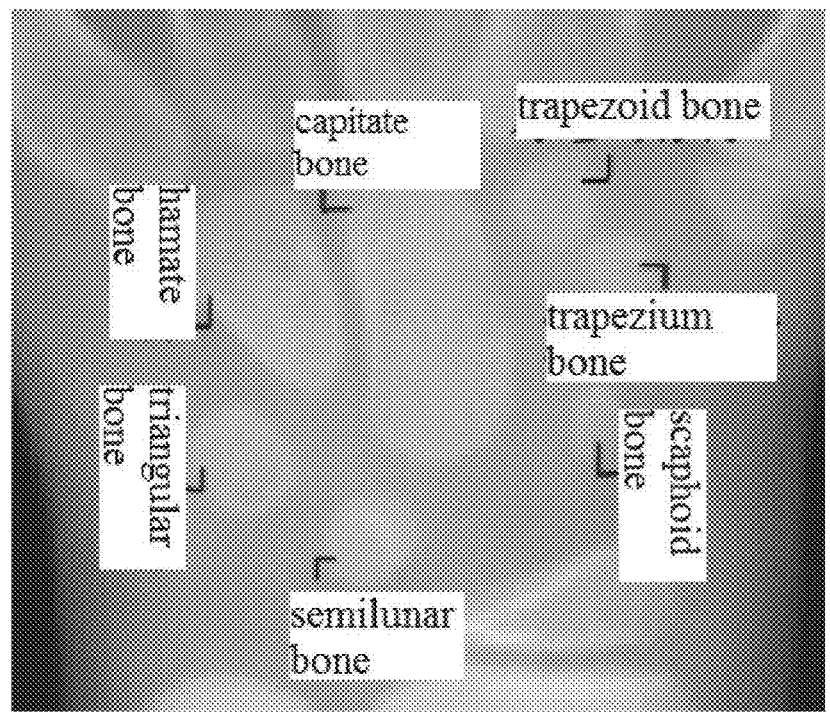
FIG. 15 is a schematic diagram of a position of each carpal bone in a carpal region according to an embodiment of the present application.

According to anatomical information, a capitate bone is the largest bone block in a carpal region in a majority of cases (there may be a case where a hamate bone is larger than the capitate bone at the initial stage of growth and development), is located below a third metacarpal bone, is a quasi-circular at the early stage, is then quasi-elliptic and finally forms an articular surface with the hamate bone, the trapezoid bone, a semilunar bone and a scaphoid bone; the hamate bone is located at an ulnar side of the capitate bone, a center-of-gravity position of the hamate bone is closer to a distal end of an arm than the center of gravity of the capitate bone in a longitudinal direction when the long axis of the capitate bone is located in a vertical direction, the hamate bone is quasi-circular at the early stage, is then quasi-triangular and finally forms an articular surface with the capitate bone, a triangular bone and the semilunar bone; the triangular bone is located at the ulnar side of the capitate bone and connected with the hamate bone and the semilunar bone, a center-of-gravity position of the triangular bone is closer to the ulna and the radius than the center of gravity of the capitate bone in a longitudinal direction, the triangular bone is quasi-circular at the early stage and forms an articular surface with the hamate bone and the semilunar bone at the later stage; the semilunar bone is located between the radius and the ulna in a horizontal direction, is closer to the ulna and the radius than the triangular bone in a longitudinal direction, is quasi-circular at the early stage and forms an articular surface with the scaphoid bone and the triangular bone at the later stage; a trapezium bone forms a radial side edge of a wrist joint, is quasi-circular at the early stage and forms an articular surface with the trapezoid bone and the semilunar bone at the later stage; and the trapezoid bone is located between the capitate bone and the trapezium bone, is a smallest carpal bone at a distal end of a carpal region, is quasi-circular at the early stage and forms an articular surface with the trapezium bone and the capitate bone at the later stage; and the scaphoid bone is located at the ulna and radius ends at the radius side, forms an edge of an arm end at the radial side of the wrist joint, is quasi-circular at the early stage and forms an articular surface with the semilunar bone, the trapezium bone, the trapezoid bone and the capitate bone at the later stage. Positions of the carpal bones in the carpal region are shown in FIG. 15.

Supervised learning is performed by applying the anatomical information to artificially recognize the segmented carpal bones, the outline and the center-of-gravity position of each carpal bone are extracted, and a Cartesian coordinate system is established by taking the center of gravity of the capitate bone as an origin, a short axis as a horizontal axis and a long axis as a longitudinal axis. Since a case where the number of the carpal bones is larger than two is only considered in the embodiment of the present application, positions of the remaining carpal bones in the Cartesian coordinate system are determined by the distance from the center of gravity of the capitate bone to the center of gravity of the hamate bone in the embodiment of the present application. A distance of the connecting line from the center of gravity of the capitate bone to the center of gravity of the hamate bone is a reference distance in the Cartesian coordinate system.

Further, it is necessary to obtain a distance from the center of gravity of each carpal bone to the center of gravity of the capitate bone and an included angle of the connecting line and the coordinate axis. The carpal anatomy priori model for showing a positional relationship among all the carpal bones in one carpal region is obtained after 500 images of the carpal bones are counted in the embodiment of the present application. The carpal anatomy priori model includes distance and angle ranges of the center-of-gravity position of each carpal bone, with the center of gravity of the capitate bone as a coordinate origin, the long axis and the short axis of the capitate bone as a longitudinal axis and a horizontal axis of a coordinate system and the distance from the center of gravity of the capitate bone to the center of gravity of the hamate bone as a reference distance $d_{ref}$, and the corresponding relationship among all the carpal bones in the carpal anatomy priori model is as shown in the following tables:

| Name of Carpal Bones | Distance from Carpal Bones to Center of Gravity of Capitate Bone | Average | Standard Deviation |
| --- | --- | --- | --- |
| Triangular Bone | 1.2 $d_{ref}$-2.0 $d_{ref}$ | 1.508 | 0.087 |
| Semilunar Bone | 1.0 $d_{ref}$-1.7 $d_{ref}$ | 1.353 | 0.101 |
| Trapezium Bone | 0.9 $d_{ref}$-1.7 $d_{ref}$ | 1.402 | 0.122 |
| Trapezoid Bone | 0.8 $d_{ref}$-1.2 $d_{ref}$ | 0.952 | 0.077 |
| Scaphoid Bone | 1.0 $d_{ref}$-1.6 $d_{ref}$ | 1.222 | 0.056 |

| Name of Carpal Bones | Included Angle of Carpal Bones and Coordinate Axis | Average | Standard Deviation |
| --- | --- | --- | --- |
| Hamate Bone | 120°-172° | 161.415° | 4.715° |
| Triangular Bone | 180°-220° | 201.963° | 7.026° |
| Semilunar Bone | 220°-258° | 238.973° | 7.351° |
| Trapezium Bone | 330°-10° | 352.786° | 6.635° |
| Trapezoid Bone | 330°-30° | 12.550° | 7.590° |
| Scaphoid Bone | 300°-335° | 311.633° | 5.673° |

Recognition of the carpal bones by utilizing the carpal anatomy priori model

1. Segmentation of the Carpal Region

Figure 16:
FIG. 16 is an initial segmentation image according to an embodiment of the present application.

The carpal region of interest is segmented by using the method to obtain an initial segmentation image of the carpal region of interest, as shown in FIG. 16.

2. Extraction of Position Information of the Third Metacarpal Bone

In an anatomical definition of the carpal bones, the capitate bone is located below the third metacarpal bone, so that the position information of the third metacarpal bone plays a role in referring to the extraction of the capitate bone. It is possible that phalanges are bent and the central axes of the phalanges and the central axes of the corresponding metacarpal bones are misaligned to affect the positioning of the metacarpal bones, so that finger portions are firstly required to be roughly removed, and information of the palm is only reserved.

A to-be-recognized image is regarded as a two-dimensional discrete function, a first order difference of the image may be regarded as a subtraction of grayscale values of two adjacent pixel points of the image, and specific formulae are as follows:

$$d_x(i,j)=I(i+1,j)-I(i,j)$$

$$d_y(i,j)=I(i,j+1)-I(i,j).$$

Figure 17A:
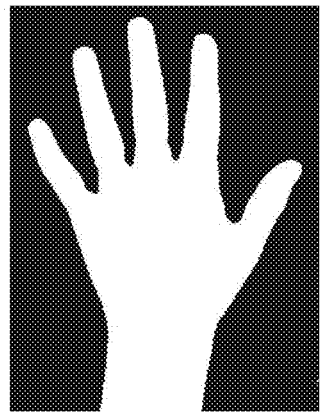
FIGS. 17a and 17b are schematic diagrams of key points of phalanges according to an embodiment of the present application.
Figure 17B:
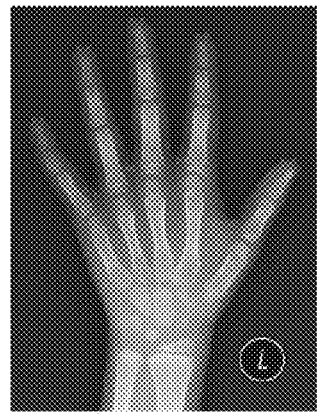

It may be derived from the formulae that the difference is performed on the binarized image. Since grayscales of pixel points inside the palm are similar and the grayscales of the pixel points at the edge of the palm are higher than those of the pixel point outside the palm, palm edge information may be obtained. If the first order difference in the X direction of the palm is only considered, at least two adjacent pixel points with the same grayscale may appear due to relatively smooth top end of the palm and relatively smooth valley points among the fingers, and thus, image difference pictures at the top end of the palm and the valley points among the fingers may be disconnected. Key points of the phalanges may be obtained by searching positions of the disconnection points, as shown in FIG. 17, wherein FIG. 17a is a palm binarized image, and FIG. 17b is a schematic diagram of key points of phalanges.

A region of the palm as well as regions of distal ends of the ulna and the radius may be roughly obtained by sequentially connecting the valley points among the fingers and two end points of the arm at the bottommost part of the palm image. Information of the ulna and the radius is not considered temporarily, proximal ends of the metacarpal bones may be superimposed when a child develops to a certain age, while each metacarpal bone may only have a rigid deformation, and therefore, the distal ends of the metacarpal bones are only reserved. An image obtained after the fingers are roughly removed is equally divided into three parts, and each of the three parts mainly includes the metacarpal bones, the carpal bones as well as the distal ends of the ulna and the radius, so that the uppermost third portion of the image obtained after the fingers are removed is reserved in the present application. White circle points in FIG. 18a are the valley points among the fingers, and arrows point at the end points of the arm at the bottommost part of the image; FIG. 18b is a palm image in which fingers are removed; and FIG. 18c is an image of distal ends of metacarpal bones.

As shown in FIG. 19b, a binarized image of the distal ends of the metacarpal bones is obtained by performing threshold segmentation operation on the extracted image of the distal ends of the metacarpal bones by applying an adaptive threshold segmentation manner of variable threshold segmentation windows. As shown in FIG. 19a, a third metacarpal reference line may be obtained by connecting a midpoint of two valley points of the third finger and a midpoint of recessed points at two sides of the located wrist; the third metacarpal bone is positioned by finding a largest region closest to the third metacarpal bone reference line in the binarized image of the distal ends of the metacarpal bones, the central axis of the third metacarpal bone is found and rotated onto a vertical direction, and meanwhile, as shown in FIG. 19c, an estimate of the width of the third metacarpal bone may be obtained, wherein the width is a range of variation of the center of gravity of the capitate bone in a horizontal direction.

3. Positioning of the Capitate Bone and Establishment of the Coordinate System

As shown in FIG. 20a, the largest region with a maximum circularity below the width of the third metacarpal bone, namely, the capitate bone, is positioned. As shown in FIG. 20b, a Cartesian coordinate system is established by taking the center of gravity of the capitate bone as an origin, a short axis as a horizontal axis and a long axis as a longitudinal axis.

4. Positioning of the Hamate Bone and the Reference Distance

Since a case where the number of the carpal bones is larger than two is only considered in the embodiment of the present application, it is relatively reliable that positions of the remaining carpal bones in the Cartesian coordinate system are determined by using the distance from the center of gravity of the capitate bone to the center of gravity of the hamate bone as the reference distance.

The hamate bone is located at the ulnar side of the capitate bone in a non-principal hand orthotopic image, and the center of gravity of the hamate bone is relatively higher than the center-of-gravity position of the capitate bone. As shown in FIG. 21a, the largest region whose circularity is largest and center-of-gravity position is not higher than the uppermost end of the capitate bone at the ulnar side of the capitate bone is positioned according to the extracted carpal information. As shown in FIG. 21b, the distance of the connecting line between the center of gravity of the capitate bone and the center of gravity of the hamate bone serves as a reference distance in coordinates of the carpal region.

4. Recognition of the Remaining Carpal Bones

Proximal ends of partial metacarpal bones, distal ends of the ulna and the radius and partial under-segmented soft tissues may also be included in the initial segmentation image obtained above by combining threshold segmentation with edges in addition to the segmented carpal bones. A region connected with the periphery of each region is determined as a non-relevant portion by analyzing a position of the region in a segmented result. Since a case where the carpal regions are not superimposed is only considered in the embodiment of the present application, the triangular bone, the semilunar bone, the trapezium bone, the trapezoid bone and the scaphoid bone are all quasi-circular, and therefore, in one embodiment of the present application, the circularity is still defined by using a formula $$\text{circularity} = \frac{4pA}{L^2}$$

(A represents the area, and L represents the perimeter), and determination is performed in the corresponding regions by applying the carpal anatomy priori model.

Each carpal bone appears in a form of a calcification point, then an ossification center is formed, and finally, the corresponding carpal bone is developed. The circularity may be relatively low due to a blurred boundary at a stage of the calcification point, so that determination results may be categorized into several conditions as follows:

1) The circularity is relatively high after the triangular bone, the semilunar bone, the trapezium bone, the trapezoid bone and the scaphoid bone develop to form relatively matured carpal bones and before the carpal bones overlap, so that it is determined whether a region in which the center of gravity is within a corresponding range, the area is larger than 26 mm$^2$ and the circularity is greater than 0.65 exists or not within corresponding angle and distance ranges of each carpal bone;

2) If the condition 1) does not exist in the corresponding region, a determination condition is changed within the corresponding range as follows: the area is greater than 0.64 mm$^2$ of the pixel point and the circularity is greater than 0.5, and it is determined whether a relatively small calcification point or ossification center exists or not; and 3) If both the conditions 1) and 2) do not exist, no corresponding carpal bones exist in the region.

FIG. 22a shows extraction of a triangular bone in an initial segmentation image, FIG. 22b shows extraction of a semilunar bone in an initial segmentation image, FIG. 22c shows extraction of a trapezium bone and a trapezoid bone in an initial segmentation image, and FIG. 22d shows extraction of a scaphoid bone in an initial segmentation image.

Boundary Optimization

An initial recognition image S1 obtained after the steps are performed may serve as an initial estimate of a carpal boundary, and a final carpal boundary is required to be optimized by using other methods. In the embodiment of the present application, boundary optimization is performed by using a marked watershed algorithm, with specific operation steps as follows:

1) Performing Gaussian processing on the carpal region of interest, making standard deviations in x and y directions be 1, and then calculating an image gradient to obtain a gradient image G as shown in FIG. 23, wherein a gradient operator in an x direction is:

| −1 | 0 | 1 |
|---|---|---| a gradient operator in a y direction is:

| −1 |
|---|
| 0 |
| 1; |

2) Negating the initial recognition image S1 to obtain a schematic diagram of a negation result as shown in FIG. 24, then calculating a distance image D as shown in FIG. 25, namely, calculating a distance from each foreground pixel p to the nearest background pixel q: D(p)=min(dist(p, q)), wherein p represents a foreground pixel, and q represents a background pixel; wherein the negating the initial recognition image S1 means that a background becomes a foreground and a foreground becomes a background in the initial recognition image S1, distance transformation on the foreground in the negated image is equivalent to distance transformation on the background in the initial recognition image S1, and dist(p, q) represents a distance from a pixel p to a pixel q, and common distances include:

Euclidean distance: $dist(p,q)=\sqrt{(p_0-q_0)^2+(p_1-q_1)^2}$;

Manhattan distance: $dist(p,q)=|p_0-q_0|+|p_1-q_1|$;

Chess square distance: $dist(p,q)=\max(|p_0-q_0|,|p_1-q_1|)$;

3) Extracting a foreground mark based on the initial recognition image S1: firstly, eroding the initial recognition image S1; performing different levels of erosion according to areas of different connected regions in the initial recognition image S1 in an erosion process; keeping the size of a structural element at 3×3 when the areas of the connected regions are smaller than 25 pixels, and keeping the size of the structural element at 5×5 when the areas of the connected regions are larger than 25 pixels; completing the erosion to obtain a segmentation image S2; and marking each connected region of the segmentation image S2, namely, setting a non-repetitive scalar value for a pixel value in each region to obtain a foreground marked image F as shown in FIG. 26a;

4) Performing watershed segmentation (ITK toolkit (http://www.itk.org/), class name: Morphological Watershed From Markers Image Filter) by taking the distance image D as an input and the foreground marked image F as a mark, extracting a watershed as a background marker, and fusing the background marker with the foreground marked image F to obtain a marked image M as shown in FIG. 26b; and 5) Performing watershed segmentation by taking the gradient image G as an input and the marked image M as a mark to obtain an optimized segmentation image as shown in FIG. 27, and using the optimized segmentation image as the carpal recognition image and outputting it, wherein an original image of the segmentation image is as shown in FIG. 8c.

FIG. 28 shows a schematic diagram of generation of a carpal recognition image according to an embodiment of the present application, wherein FIG. 28a is a carpal region of interest, FIG. 28b is a binarized image with irrelevant information removed of a carpal region of interest, and FIG. 28c is a binarized image of a carpal region subjected to boundary optimization by using a watershed algorithm.

By combining threshold segmentation with edge extraction, the embodiment of the present application reserves respective advantages of two methods, and avoids under-segmentation or over-segmentation in carpal segmentation due to exclusive use of one method, thereby obtaining high-accuracy initial segmentation of the carpal bones. A boundary is optimized by using the marked watershed algorithm on this basis, which effectively overcomes the defect that a Canny boundary operator is required to perform threshold processing on edge strength. Bones and soft tissues in the carpal region of interest may be relatively accurately segmented, and a result may be used for further analyzing the carpal bones. Based on a segmentation result, supervised recognition and positioning are performed on the carpal bones in combination with anatomical knowledge, the carpal anatomy priori model capable of guiding accurate recognition of the carpal bones is provided, and the carpal anatomy priori model is applied to a carpal recognition process and has a certain robustness.

The segmentation and recognition method provided by the embodiment of the present application is favorably embodied in cases where the area of the carpal bones is relatively small and the contrast between the carpal bones and the soft tissues around the carpal bones is relatively low, which proves the effectiveness of the segmentation and recognition method provided by the embodiment of the present application.

In the embodiment of the present application, besides the carpal bones are segmented and recognized by using the abovementioned method, boundary optimization on the initial carpal segmentation may be performed by adopting an active outline model or level set method in addition to a marker-based watershed algorithm, and the Canny boundary operator may be replaced with other boundary operators such as Laplacian of the Gaussian (LOG) with excellent performances. Further, regional information may be processed by adopting other regional segmentation methods such as a clustering method and a deep learning method with excellent performances in addition to an existing local grayscale threshold method, and detailed descriptions will be omitted herein.

Figure 29:
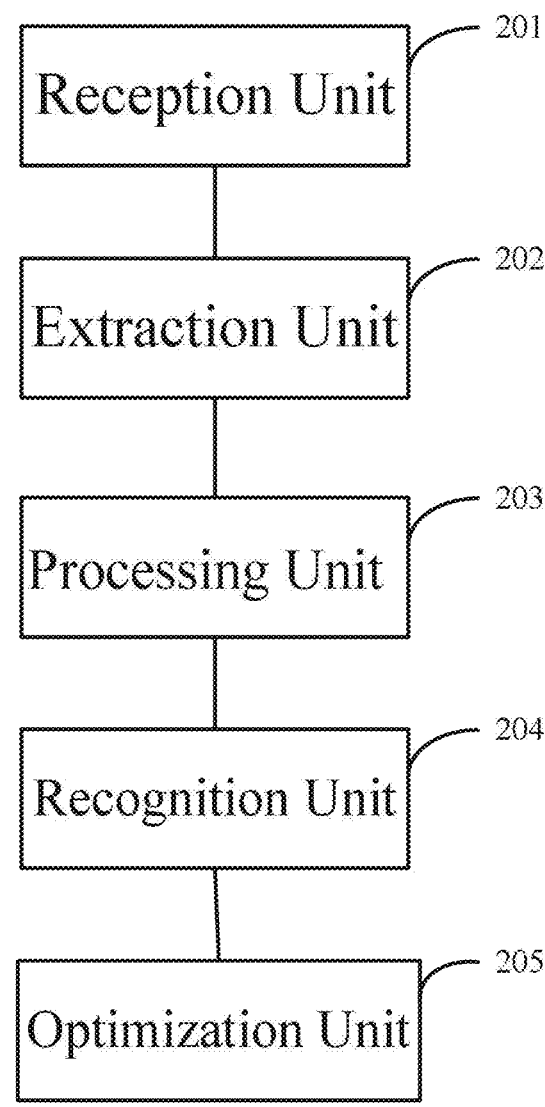
FIG. 29 is a schematic structural diagram of a carpal segmentation and recognition system according to an embodiment of the present application.

The present application further provides a carpal segmentation and recognition system as shown in FIG. 29, including:

A reception unit 201, which is configured to receive an image to be recognized, wherein the image to be recognized is a child orthotopic wrist X-ray image in which carpal bones are not completely present or the carpal bones are completely present but there is no overlap between the carpal bones;

An extraction unit 202, which is configured to perform binarization on the image to be recognized to obtain a palm binarized image, and extract a carpal region of interest in the image to be recognized according to the palm binarized image;

A processing unit 203, which is configured to perform threshold segmentation on the carpal region of interest based on an adaptive threshold segmentation manner of variable threshold segmentation windows, and extract edge information of the carpal region of interest based on an edge detection manner, and combine a binarized image obtained by performing the threshold segmentation with the extracted edge information to obtain an initial segmentation image;

A recognition unit 204, which is configured to perform carpal recognition on the initial segmentation image by using a carpal anatomy priori model to obtain an initial recognition image including information of each carpal bone; and An optimization unit 205, which is configured to perform boundary optimization on the initial recognition image, and output a carpal recognition image obtained after the boundary optimization is performed.

Further, the extraction unit 202 is specifically configured to:

Count a grayscale histogram of the image to be recognized, and calculate a valley point whose slope is largest from the valley points to their adjacent peaks in the grayscale histogram;

Perform binarization on the image to be recognized with a grayscale value of the valley point whose slope is largest as a threshold to obtain a palm binarized image;

Extract a palm outline in the palm binarized image and solve an approximate polygon of the palm outline;

Obtain a convex hull of the approximate polygon, wherein a plurality of concave portions are formed between the convex hull and the approximate polygon;

Find a point at which each concave portion is at a maximum distance from the adjacent convex hull, and use the point at which each concave portion is at the maximum distance from the adjacent convex hull as a recessed point of the concave portion;

Search the recessed point according to a preset direction from an interception point at the lowermost end of the image to be recognized to find a first recessed point and the last recessed point; and Make a circumscribed circle by using a straight segment (the straight segment is a wrist line) in which the first recessed point and the last recessed point intersect a palm region as a diameter, and make a circumscribed square of the circumscribed circle, with the circumscribed square as the carpal region of interest.

Further, any pixel in the carpal region of interest is represented by (x, y), a center of a threshold segmentation window corresponding to the pixel point is located at (x, y), and the threshold segmentation window has a width of W(x, y) and a height of H(x, y), a processing unit 203 performs threshold segmentation on the carpal region of interest through the adaptive threshold segmentation manner of the variable threshold segmentation windows, and the adaptive threshold segmentation manner of the variable threshold segmentation windows includes:

Finding a maximum standard deviation $sd_{max}$ of grayscales in all threshold segmentation windows in the carpal region of interest;

For each pixel (x, y), finding a minimum threshold segmentation window that makes a standard deviation sd of grayscales in the threshold segmentation windows centered on each pixel point (x, y) not less than 0.6*$sd_{max}$, wherein the minimum threshold segmentation window satisfies W(x, y)=H(x, y);

Calculating a segmentation threshold of each threshold segmentation window by a formula $$T(x, y) = m(x, y) * \left(1 + k * \frac{sd}{1.2 * sd_{max}}\right),$$

wherein m(x, y) represents a grayscale average of the threshold segmentation window, k represents a constant between [0.04, 0.08], and T(x, y) represents Grayscale threshold of the pixel (x, y); and Performing threshold segmentation on the carpal region of interest according to the segmentation threshold to obtain a binarized image.

Further, the step of performing edge extraction on the carpal region of interest by the processing unit 203 includes:

Smoothing the carpal region of interest by using a Gaussian filter with a size of 3*3 and a σ of 1;

Calculating a gradient magnitude and a gradient direction of the smoothed carpal region of interest by using a Sobel operator of 5*5;

Performing non-maximal suppression on the gradient magnitude;

Testing and joining edges by using a double-threshold algorithm to obtain initial edge information; and Analyzing areas and lengths of all the segment in the initial edge information, and deleting segments whose areas are smaller than a preset value to obtain the edge information.

Further, the processing unit 203 is further configured to:

If there is over-segmentation in the binarized image, determine whether a pixel in which an edge in the edge information is located serves as a foreground in the binarized image, and if the pixel serves as the foreground, set the pixel in which the edge is located as a background, and perform hole filling on an image obtained after the binarized image is combined with the edge information, and erode an image obtained after the hole filling is performed to obtain the initial segmentation image; and If there is under-segmentation in the binarized image, determine whether a pixel in which an edge in the edge information is located serves as a background in the binarized image, and if the pixel serves as the background, set the pixel in which the edge is located as a foreground to complete edge addition, perform hole filling on the binarized image subjected to the edge addition, and erode a binarized image obtained after the hole filling is performed to obtain the initial segmentation image.

Further, the carpal anatomy priori model includes distance and angular ranges of a centre-of-gravity position of each carpal bone, with the center of gravity of a capitate bone as a coordinate origin, a long axis and a short axis of the capitate bone as a longitudinal axis and a horizontal axis of a coordinate system and a distance between the center of gravity of the capitate bone and the center of gravity of a hamate bone as a reference distance, the recognition unit 204 is specifically configured to:

Perform first-order difference on the palm binarized image to obtain palm edge information, wherein the palm edge information includes valley point information of finger apexes and finger tips;

According to valley points among fingers and two end points of an arm at the bottommost part of the palm binarized image, intercept regions of a palm and distal ends of the ulna and the radius from the image to be recognized;

Equally divide the regions of the palm and the distal ends of the ulna and the radius into three parts from top to bottom, and take the uppermost third portion as an image of a distal end of a metacarpal bone;

Perform a threshold segmentation operation on the image of the distal end of the metacarpal bone by using an adaptive threshold segmentation manner of variable threshold segmentation windows to obtain a binarized image of the distal end of the metacarpal bone;

Determine a midpoint of two valley points of the third finger according to the palm edge information, connect the midpoint of the two valley points of the third finger with a midpoint of a connecting line of a first recessed point and the last recessed point to obtain a third reference line of the metacarpal bone;

Search a largest region closest to the third reference line of the metacarpal bone in the binarized image of the distal end of the metacarpal bone, use the largest region closest to the third reference line of the metacarpal bone as a third metacarpal bone, and find a central axis of the third metacarpal bone, rotate the central axis onto a vertical direction to obtain a width of the third metacarpal bone, and use a width of the third metacarpal bone as a range of variation of the center of gravity of the capitate bone in a horizontal direction;

Determine, in the initial segmentation image, a largest region with a maximum circularity below a width of the third metacarpal bone, and use the largest region with the maximum circularity as the capitate bone;

Establish a Cartesian coordinate system by taking the center of gravity of the capitate bone as an origin, a short axis of the capitate bone as a horizontal axis and a longitudinal axis of the capitate bone as a longitudinal axis;

Use a largest region whose centre-of-gravity position is not higher than the uppermost end of the capitate bone and circularity is maximal at the ulnar side of the capitate bone on the initial segmentation image as the hamate bone, determine a distance of a connecting line between the center of gravity of the capitate bone and the center of gravity of the hamate bone, and use the distance of the connecting line as a reference distance of the Cartesian coordinate system; and Perform carpal recognition on the initial segmentation image according to the carpal anatomy priori model, the Cartesian coordinate system and the reference distance to obtain an initial recognition image including information of each carpal bone.

Further, the optimization unit 205 is specifically configured to:

Perform Gaussian smoothing on the carpal region of interest, and calculate an image gradient of the carpal region of interest subjected to Gaussian smoothing to obtain a gradient image;

Negate the initial recognition image, and perform distance transformation on a foreground of the image obtained by the negation to obtain a distance image;

Erode the initial recognition image to obtain a segmentation image, and set a non-repetitive scalar value for each pixel value in each connected region of the segmentation image to obtain a foreground marked image;

Perform watershed segmentation by taking the distance image as an input and use the foreground marked image as a marker, extract a watershed, and fuse a background marker with the foreground marked image by using the watershed as the background marker to obtain a marked image; and Perform watershed segmentation by using the gradient image as an input and using the marked image as a marker to perform to obtain an optimized segmentation image, and use the optimized segmentation image as a carpal recognition image and output it.

Another embodiment of the present application further provides a terminal for performing a carpal segmentation and recognition method. For the convenience of description, only parts related to the embodiment of the present application are shown. Details that are not disclosed refer to a method section of the embodiment of the present application. The terminal may be a terminal for performing a segmentation and recognition operation on carpal bones, including a mobile phone, a tablet computer, a PDA (Personal Digital Assistant), a POS (Point of Sales), a desktop computer, a car computer, a smart TV, and the like.

The terminal includes one or more processors, a memory, and one or more programs (modules). Among them, the one or more programs (modules) are stored in the memory, and when the one or more programs are executed by the one or more processors, the processor performs the following operations: performing threshold segmentation on a carpal region of interest on a child orthotopic wrist X-ray image based on an adaptive threshold segmentation manner of variable threshold segmentation windows, and extracting edge information of the carpal region of interest based on an edge detection manner;

Combining a binarized image obtained by performing the threshold segmentation with the extracted edge information to obtain an initial segmentation image;

Performing carpal recognition on the initial segmentation image by using a carpal anatomy priori model to obtain an initial recognition image including information of each carpal bone; and Performing boundary optimization on the initial recognition image, and outputting a carpal recognition image obtained after the boundary optimization is performed.

The above is only preferred embodiments of the present application, and is not intended to limit the present application. Any modifications, equivalent substitutions and improvements made within the spirit and principle of the present application should be included in a protective scope of the present application.

What is claimed is:

1. A carpal segmentation and recognition method, comprising:

performing threshold segmentation on a carpal region of interest on a child orthotopic wrist X-ray image based on an adaptive threshold segmentation manner of variable threshold segmentation windows, and extracting edge information of the carpal region of interest based on an edge detection manner;

combining a binarized image obtained by performing the threshold segmentation with the extracted edge information to obtain an initial segmentation image;

performing carpal recognition on the initial segmentation image by using a carpal anatomy priori model to obtain an initial recognition image comprising information of each carpal bone; and performing boundary optimization on the initial recognition image, and outputting a carpal recognition image obtained after the boundary optimization is performed;

wherein the performing boundary optimization on the initial recognition image and outputting a carpal recognition image obtained after the boundary optimization is performed comprises:

performing Gaussian smoothing on the carpal region of interest, and calculating an image gradient of the carpal region of interest subjected to the Gaussian smoothing to obtain a gradient image;

negating the initial recognition image, and performing distance transformation on a foreground of an image obtained by the negation to obtain a distance image;

eroding the initial recognition image to obtain a segmentation image, and setting a non-repetitive scalar value for each pixel value in each connected region of the segmentation image to obtain a foreground marked image;

performing watershed segmentation by taking the distance image as an input and using the foreground marked image as a marker, extracting a watershed, and fusing a background marker with the foreground marked image by using the watershed as the background marker to obtain a marked image; and performing watershed segmentation by using the gradient image as an input and using the marked image as a marker to obtain an optimized segmentation image, and using the optimized segmentation image as the carpal recognition image and outputting it.

2. The segmentation and recognition method of claim 1, wherein any pixel in the carpal region of interest is represented by (x, y), a center of a threshold segmentation window corresponding to a pixel point is located at (x, y), the threshold segmentation window has a width of W(x, y) and a height of H(x, y), the performing threshold segmentation on the carpal region of interest by an adaptive threshold segmentation manner of variable threshold segmentation windows comprises:

finding, in the carpal region of interest, a maximum standard deviation $sd_{max}$ of grayscales in all possible threshold segmentation windows;

for each pixel (x, y), finding a smallest threshold segmentation window that makes a standard deviation sd of grayscales in the threshold segmentation windows centered on each pixel point (x, y) not less than $0.6*sd_{max}$, wherein the smallest threshold segmentation window satisfies W(x, y)=H(x, y);

calculating a segmentation threshold of each threshold segmentation window by a formula $$T(x, y) = m(x, y) * \left(1 + k * \frac{sd}{1.2 * sd_{max}}\right),$$

wherein m(x, y) represents a grayscale average of the threshold segmentation windows, k represents a constant between 0.04 and 0.08, and T(x, y) represents a grayscale threshold of the pixel (x, y); and performing threshold segmentation on the carpal region of interest according to the segmentation threshold to obtain a binarized image.

3. The segmentation and recognition method of claim 1, wherein the extracting edge information of the carpal region of interest based on an edge detection manner comprises:

smoothing the carpal region of interest by using a Gaussian filter with a size of 3*3 and a σ of 1;

calculating a gradient amplitude and a gradient direction of the smoothed carpal region of interest by using a Sobel operator of 5*5;

performing non-maximum suppression on the gradient amplitude;

testing and joining edges by using a double-threshold algorithm to obtain initial edge information; and analyzing areas and lengths of all segments in the initial edge information, and deleting segments whose areas are smaller than a preset value to obtain the edge information.

4. The segmentation and recognition method of claim 3, wherein the combining a binarized image obtained by performing the threshold segmentation with the extracted edge information to obtain an initial segmentation image comprises:

if there is over-segmentation in the binarized image, determining a pixel in which an edge in the edge information serves as a foreground in the binarized image or not, and if the pixel serves as the foreground, setting the pixel in which the edge is located as a background, performing hole filling on an image obtained after the binarized image is combined with the edge information, and eroding an image obtained after the hole filling is performed o obtain the initial segmentation image; and if there is under-segmentation in the binarized image, determining a pixel in which an edge in the edge information serves as a background in the binarized image or not, and if the pixel serves as the background, setting the pixel in which the edge is located as a foreground to complete edge addition, performing hole filling on a binarized image subjected to the edge addition, and eroding an image obtained after the hole filling is performed to obtain the initial segmentation image.

5. The segmentation and recognition method of claim 1, wherein the carpal anatomy priori model comprises distance and angle ranges of a center-of-gravity position of each carpal bone, with the center of gravity of a capitate bone as a coordinate origin, a long axis and a short axis of the capitate bone as a longitudinal axis and a horizontal axis of a coordinate system and a distance from the center of gravity of the capitate bone to the center of gravity of a hamate bone as a reference distance:

before performing threshold segmentation on a carpal region of interest based on a adaptive threshold segmentation manner of variable threshold segmentation windows and extracting edge information of the carpal region of interest based on an edge detection manner, further comprising:

receiving an image to be recognized, wherein the image to be recognized is a child orthotopic wrist X-ray image in which carpal bones are not completely present or the carpal bones are completely present but there is no overlap between the carpal bones;

performing binarization on the image to be recognized to obtain a palm binarized image, and extracting the carpal region of interest in the image to be recognized according to the palm binarized image;

the performing carpal recognition on the initial segmentation image by using a carpal anatomy priori model to obtain an initial recognition image comprising information of each carpal bone comprises:

performing a first-order difference on the palm binarized image to obtain palm edge information, wherein the palm edge information comprises valley point information of finger apexes and finger tips;

according to valley points among fingers and two end points of an arm at the bottommost part of the palm binarized image, intercepting regions of a palm and distal ends of the ulna and the radius from the image to be recognized;

equally dividing the regions of the palm and the distal ends of the ulna and the radius into three parts from top to bottom, and taking the uppermost third portion as an image of a distal end of a metacarpal bone;

performing a threshold segmentation operation on the image of the distal end of the metacarpal bone by using an adaptive threshold segmentation manner of variable threshold segmentation windows to obtain a binarized image of the distal end of the metacarpal bone;

determining a midpoint of two valley points of the third finger according to the palm edge information, connecting the midpoint of the two valley points of the third finger with a midpoint of a connecting line between a first recessed point and the last recessed point to obtain a third metacarpal reference line;

searching a largest region closest to the third metacarpal reference line in the binarized image of the distal end of the metacarpal bone, using the largest region closest to the third metacarpal reference line as a third metacarpal bone, finding a central axis of the third metacarpal bone, rotating the central axis onto a vertical direction to obtain a width of the third metacarpal bone, and using a width of the third metacarpal bone as a range of variation of the center of gravity of the capitate bone in a horizontal direction;

determining, in the initial segmentation image, a largest region with the maximum circularity below a width of the third metacarpal bone, and using the largest region with the maximum circularity as the capitate bone;

establishing a Cartesian coordinate system by taking the center of gravity of the capitate bone as an origin, a short axis of the capitate bone as a horizontal axis and a long axis of the capitate bone as a longitudinal axis;

using a largest region whose centre-of-gravity position is not higher than the uppermost end of the capitate bone and circularity is maximal at the ulnar side of the capitate bone on the initial segmentation image as the hamate bone, determining a distance of a connecting line between the center of gravity of the capitate bone and the center of gravity of the hamate bone and using the distance of the connecting line as a reference distance of the Cartesian coordinate system; and performing carpal recognition on the initial segmentation image according to the carpal anatomy priori model, the Cartesian coordinate system and the reference distance to obtain an initial recognition image comprising information of each carpal bone.

6. The segmentation and recognition method of claim 5, wherein $$\text{circularity} = \frac{4pA}{L^2},$$

wherein A represents an area of a region whose circularity is to be calculated, and L represents a perimeter of the region whose circularity is to be calculated.

7. A carpal segmentation and recognition system, comprising:
a processing unit, which is configured to perform threshold segmentation on a carpal region of interest on a child orthotopic wrist X-ray image based on an adaptive threshold segmentation manner of variable threshold segmentation windows, and extract edge information of the carpal region of interest based on an edge detection manner, combine a binarized image obtained by performing the threshold segmentation with the extracted edge information to obtain an initial segmentation image;
a recognition unit, which is configured to perform carpal recognition on the initial segmentation image by using a carpal anatomy priori model to obtain an initial recognition image comprising information of each carpal bone; and
an optimization unit, which is configured to perform boundary optimization on the initial recognition image, and output a carpal recognition image obtained after the boundary optimization is performed;
wherein the optimization unit is specifically configured to:
perform Gaussian smoothing on the carpal region of interest, and calculate an image gradient of the carpal region of interest subjected to the Gaussian smoothing to obtain a gradient image;
negate the initial recognition image, and perform distance transformation on a foreground of an image obtained by the negation to obtain a distance image;
erode the initial recognition image to obtain a segmentation image, and set a non-repetitive scalar value for each pixel value in each connected region of the segmentation image to obtain a foreground marked image;
perform watershed segmentation by taking the distance image as an input and use the foreground marked image as a marker, extract a watershed, and fuse a background marker with the foreground marked image by using the watershed as the background marker to obtain a marked image; and
perform watershed segmentation by using the gradient image as an input and use the marked image as a marker to obtain an optimized segmentation image, and use the optimized segmentation image as the carpal recognition image and output it.

8. The segmentation and recognition system of claim 7, wherein any pixel in the carpal region of interest is represented by (x, y), a center of a threshold segmentation window corresponding to a pixel point is located at (x, y), the threshold segmentation window has a width of W(x, y) and a height of H(x, y), the processing unit is specifically configured to:
find, in the carpal region of interest, a maximum standard deviation $sd_{max}$ of grayscales in all possible threshold segmentation windows;
for each pixel (x, y), find a smallest threshold segmentation window that makes a standard deviation sd of grayscales in the threshold segmentation windows centered on each pixel point (x, y) not less than $0.6*sd_{max}$, wherein the smallest threshold segmentation window satisfies W(x, y)=H(x, y);
calculate a segmentation threshold of each threshold segmentation window by a formula $$T(x, y) = m(x, y) * \left(1 + k * \frac{sd}{1.2 * sd_{max}}\right),$$

wherein m(x, y) represents a grayscale average of the threshold segmentation windows, k represents a constant between 0.04 and 0.08, and T(x, y) represents a grayscale threshold of the pixel (x, y); and
perform threshold segmentation on the carpal region of interest according to the segmentation threshold to obtain a binarized image.

9. The segmentation and recognition system of claim 8, wherein the processing unit is further configured to:
smooth the carpal region of interest by using a Gaussian filter with a size of 3*3 and a σ of 1;
calculate a gradient amplitude and a gradient direction of the smoothed carpal region of interest by using a Sobel operator of 5*5;
perform non-maximum suppression on the gradient amplitude;
test and join edges by using a double-threshold algorithm to obtain initial edge information; and
analyze areas and lengths of all segments in the initial edge information, and delete segments whose areas are smaller than a preset value to obtain the edge information.

10. The segmentation and recognition system of claim 9, wherein the processing unit is further configured to:
if there is over-segmentation in the binarized image, determine a pixel in which an edge in the edge information serves as a foreground in the binarized image or not, and if the pixel serves as the foreground, set the pixel in which the edge is located as a background, perform hole filling on an image obtained after the binarized image is combined with the edge information, and erode an image obtained after the hole filling is performed to obtain the initial segmentation image; and if there is under-segmentation in the binarized image, determine a pixel in which an edge in the edge information serves as a background in the binarized image or not, and if the pixel serves as the background, set the pixel in which the edge is located as a foreground to complete edge addition, perform hole filling on a binarized image subjected to the edge addition, and erode an image obtained after the hole filling is performed to obtain the initial segmentation image.

11. The segmentation and recognition system of claim 7, wherein the carpal anatomy priori model comprises distance and angle ranges of a center-of-gravity position of each carpal bone, with the center of gravity of a capitate bone as a coordinate origin, a long axis and a short axis of the capitate bone as a longitudinal axis and a horizontal axis of a coordinate system and a distance from the center of gravity of the capitate bone to the center of gravity of the hamate bone as a reference distance, and the segmentation and recognition system further comprises:

a reception unit, which is configured to receive an image to be recognized, wherein the image to be recognized is a child orthotopic wrist X-ray image in which carpal bones are not completely present or the carpal bones are completely present but there is no overlap between the carpal bones;

an extraction unit, which is configured to perform binarization on the image to be recognized to obtain a palm binarized image, and extract a carpal region of interest in the image to be recognized according to the palm binarized image;

the recognition unit is specifically configured to:

perform a first-order difference on the palm binarized image to obtain palm edge information, wherein the palm edge information comprises valley point information of finger apexes and finger tips;

according to valley points among fingers and two end points of an arm at the bottommost part of the palm binarized image, intercept regions of a palm and distal ends of the ulna and the radius from the image to be recognized;

equally divide the regions of the palm and the distal ends of the ulna and the radius into three parts from top to bottom, and take the uppermost third portion as an image of a distal end of a metacarpal bone;

perform a threshold segmentation operation on the image of the distal end of the metacarpal bone by using an adaptive threshold segmentation manner of variable threshold segmentation windows to obtain a binarized image of the distal end of the metacarpal bone;

determine a midpoint of two valley points of the third finger according to the palm edge information, connect the midpoint of the two valley points of the third finger with a midpoint of a connecting line between a first recessed point and the last recessed point to obtain a third metacarpal reference line;

search a largest region closest to the third metacarpal reference line in the binarized image of the distal end of the metacarpal bone, use the largest region closest to the third metacarpal reference line as a third metacarpal bone, find a central axis of the third metacarpal bone, rotate the central axis onto a vertical direction to obtain a width of the third metacarpal bone, and using a width of the third metacarpal bone as a range of variation of the center of gravity of the capitate bone in a horizontal direction;

determine, in the initial segmentation image, a largest region with the maximum circularity below a width of the third metacarpal bone, and use the largest region with the maximum circularity as a capitate bone;

establish a Cartesian coordinate system by taking the center of gravity of the capitate bone as an origin, a short axis of the capitate bone as a horizontal axis and a long axis of the capitate bone as a longitudinal axis;

use a largest region whose centre-of-gravity position is not higher than the uppermost end of the capitate bone and circularity is maximal at the ulnar side of the capitate bone on the initial segmentation image as the hamate bone, determine a distance of a connecting line between the center of gravity of the capitate bone and the center of gravity of the hamate bone and use the distance of the connecting line as a reference distance of the Cartesian coordinate system; and perform carpal recognition on the initial segmentation image according to the carpal anatomy priori model, the Cartesian coordinate system and the reference distance to obtain an initial recognition image comprising information of each carpal bone.

12. A terminal, comprising a memory, a processor and a computer program stored on the memory and running on the processor, wherein the processor implements various steps in the carpal segmentation and recognition method according to claim 1 when executing the computer program.

* * * * *